US 6,709,269 B1

(12) United States Patent
Altshuler (10) Patent No.: US 6,709,269 B1
(45) Date of Patent: Mar. 23, 2004

(54) APPARATUS AND METHOD FOR THE PROCESSING OF SOLID MATERIALS, INCLUDING HARD TISSUES (76) Inventor: Gregory B. Altshuler, 8R Fernbanks Rd., Wilmington, MA (US) 01887

(*) Notice: Subject to any disclaimer, the term of this patent is extended or adjusted under 35 U.S.C. 154(b) by 0 days.

(21) Appl. No.: 09/549,406

(22) Filed: Apr. 14, 2000

(51) Int. Cl.⁷ .............................................. A61C 3/00
(52) U.S. Cl. ........................ 433/29; 433/215; 606/12; 250/492
(58) Field of Search ....................... 433/29, 215; 606/3, 606/12, 13, 15

(56) References Cited

U.S. PATENT DOCUMENTS

| | | | |
|---|---|---|---|
| 4,503,853 A | 3/1985 | Sadayasu et al. | |
| 5,020,995 A | * 6/1991 | Levy | 433/215 |
| 5,060,527 A | 10/1991 | Burgess | |
| 5,199,870 A | 4/1993 | Steiner et al. | |
| 5,257,935 A | 11/1993 | Vassiliadis et al. | |
| 5,267,856 A | * 12/1993 | Wolbarsht et al. | 433/29 |
| 5,334,016 A | 8/1994 | Goldsmith et al. | |
| 5,401,171 A | 3/1995 | Paghdiwala | |
| 5,409,376 A | 4/1995 | Murphy | |
| 5,456,603 A | * 10/1995 | Kowalyk et al. | 433/215 |
| 5,554,029 A | * 9/1996 | Kowalyk et al. | 433/215 |
| 5,636,983 A | 6/1997 | Shoji et al. | |
| 5,734,765 A | * 3/1998 | Artjushenko et al. | 385/31 |
| 5,746,596 A | 5/1998 | Gallant et al. | |
| 5,752,948 A | 5/1998 | Tankovich et al. | |
| 5,785,703 A | 7/1998 | Goodman et al. | |
| 5,800,165 A | 9/1998 | Kirsch et al. | |
| 5,873,875 A | 2/1999 | Altshuler | |
| 5,957,691 A | * 9/1999 | Goodman et al. | 433/215 |
| 5,968,035 A | 10/1999 | Goodman et al. | |
| 6,083,218 A | * 7/2000 | Chou | 606/10 |
| 6,137,110 A | * 10/2000 | Pellin et al. | 250/423 |
| 6,162,055 A | 12/2000 | Montgomery et al. | |
| 6,270,342 B1 | 8/2001 | Neuberger et al. | |

FOREIGN PATENT DOCUMENTS

| | | |
|---|---|---|
| EP | 0 976 421 A1 | 2/2000 |
| SU | 1593669 A | 9/1990 |
| WO | WO 00/62694 A1 | 10/2000 |

OTHER PUBLICATIONS

G.B. Altshuler, "Human tooth in low and high intensive light fields," Proc. SPIE, vol. 2623, pp. 68–81, 1996.

* cited by examiner

Primary Examiner—Kevin Shaver
Assistant Examiner—Melba Bumgarner
(74) Attorney, Agent, or Firm—Wolf, Greenfield & Sacks, P.C.

(57) ABSTRACT

A method and apparatus are provided for processing solid materials in general, and of dental material in particular, which involves applying radiation from a laser or other suitable pulsed radiation source to process and to preferably ablate the material in a region of processing thereof. Particles of ablation are generated by the radiation from the area of processing and/or other source(s) which are directed to the area of processing to further process the material. Particles adhering to a tip through which the radiation is applied, to a reflector or other surfaces adjacent the region of processing at the end of each radiation pulse may be ablated and accelerated back to the region of processing by the next pulse. Ablation particles may also be obtained from the ablation of the tip, from a strip of material through which radiation passes before reaching the region of processing or from other sources. Mechanism may also be provided for cooling the surface of the material in the region of processing between radiation pulses and/or during such pulses and/or for facilitating removal of particles in the area between the chip and the region of processing between radiation pulses.

53 Claims, 7 Drawing Sheets

APPARATUS AND METHOD FOR THE PROCESSING OF SOLID MATERIALS, INCLUDING HARD TISSUES

FIELD OF THE INVENTION

The invention concerns methods and apparatus for the processing of solid materials, including hard tissues, metals, ceramics, crystals, glass, certain plastics, etc. and uses thereof in dentistry, surgery, orthopedics and other material processing applications.

BACKGROUND OF THE INVENTION

Laser radiation is widely used for the processing of hard materials: drilling, cutting, modification of properties and other operations. The mechanism for destruction of hard materials under the influence of laser radiation involves the absorption of laser energy, which results in heating, melting and evaporation of the materials. Other mechanisms involve absorption of radiation by strongly absorptive materials (chromophores), their heating and the breaking of the material because of pressure around the absorptive materials. The process of laser destruction of materials under the influence of short pulses (generally pulses shorter than the thermal relaxation time of the target) is sometimes called laser ablation. In order to reach the maximum efficiency of material removal, the wavelength of the laser radiation is selected to be within the range of maximum absorption for the absorptive material. Depending on the properties of the material, the optimum parameters of laser radiation are selected. These parameters include the wavelength, the pulse duration, the diameter of laser beam spot, and the energy or power. Laser destruction of hard materials has a lot of advantages; however, in many cases it is slower than drilling or other mechanical methods of processing.

Russian certificate of invention USSR N 1593669, published Sep. 23, 1990, discusses the removal of hard tooth tissues by radiation with 2.94 $\mu$m wavelength (Er:YAG laser), with pulse duration of 100–500 $\mu$s and with energy of 0.5–1 J. U.S. Pat. No. 5,257,935 issued Oct. 2, 1993 proposes a laser with a wavelength within the range 1.5–3.5 $\mu$m, in particular 2.94 $\mu$m, for the same objective. The radiation in this device is delivered from the laser to the processing zone using an optical fiber connected to a tip in contact with a tooth surface. The disadvantage of this method and apparatus is that the speed of material removal is slower than for high-speed drills. Its use therefore results in an increase in procedure duration. However, the laser procedure is in most cases painless and does not require anesthesia. The laser processing is also less traumatic.

In the apparatus and method disclosed in the U.S. Pat. No. 5,409,376, issued Apr. 25, 1995, mechanical drilling is combined with laser drilling in order to increase the speed of processing. However, this increases the price of both the treatment process and the drilling apparatus. Further, when used for the processing of dental tissues, it results in the loss of the main advantages of laser processing—absence of pain and low danger of trauma.

A major disadvantage of the techniques discussed above is insufficient utilization of the laser energy. This is due to the fact that a significant part of the laser pulse energy absorbed by the processed material is transformed to mechanical energy of particles leaving the zone of processing, this energy being uselessly spent in heating the environment. Similar issues can arise when a laser is used to ablate solid materials other than dental tissue.

SUMMARY OF THE INVENTION

In accordance with the above, this invention, in accordance with a first aspect thereof, provides a method of processing a solid material which includes exposing the material to pulsed radiation with an energy above an ablation threshold for the material; and returning or otherwise directing particles of ablated material to a region of processing of the material to further influence material processing. Some of the particles of ablated material will be deposited on a surface adjacent the region of processing, the method including returning these deposited particle to the region of processing in response to the next radiation pulse to further process the material. While the region of processing is the source of the particles of ablated material for a preferred embodiment, other sources of particles may also exist, either in addition to or instead of the preferred source, which particles can be delivered to the region of processing for the further processing of the material. Potential sources for such added material include a tip through which radiation is delivered, reflectors surrounding the tip and/or an additional piece of material positioned between the radiation source and the region of processing which may be ablated by radiation passing therethrough to produce accelerated particles. For a preferred embodiment, the material being processed is a dental material, for example dental enamel, dentin, bone, stain, filling material, cementum and the like. For such embodiments, the pulsed radiation is preferably from a laser with a wavelength within one of the bands 1.9–2.1 $\mu$m, 2.65–3.5 $\mu$m, 5.6–7.5 $\mu$m, and 8.5–11 $\mu$m; a duration of 0.0001–10000 $\mu$s (preferably 1–500 $\mu$s); and an energy density of 0.5–500 J/cm$^2$. The method may also include cooling the region of processing of the material and/or removing particles from an area between a source of the pulsed radiation and the region of processing, these steps preferably being performed between pulses of the radiation for some embodiments. For another embodiment, air is first applied to the region of processing to clean at least the area. A light water spray or mist is then applied to both cool the area and to be ablated, the laser or other radiation source being fired during the applications of the mist. After the firing of the radiation source, the misting or a stronger water spray may be applied to cool the region of processing. While the three steps indicated above are preferably used together, for some embodiments, one or more of these steps may be individually performed.

The invention also includes a device for processing a solid material which includes a source of pulsed radiation and a system for delivering radiation from the source through a tip to a region of processing, the tip including an end for delivering radiation to at least one particle source, the radiation accelerating particles from the particle source, which particles are accelerated and/or reflected to a region of processing on the surface of the solid material to influence the processing thereof. For preferred embodiments, the particle source is the region of processing on the surface of the solid material, the radiation ablating the surface to create particles of ablation accelerated away from the surface, at least some of these particles being reflected back to the region of processing by at least one of the tip and a reflector surrounding the tip to further process the surface. The radiation and the reflected particles may impinge on substantially the same point in a region of processing or they may impinge on different points in this region to increase the area being processed.

At the end of at least some radiation pulses, some particles of ablation may adhere to the tip or other surfaces adjacent the area of processing, and these adhered particles may serve as an additional particle source for a subsequent radiation pulse, the adhered particles being ablated by such radiation pulse so as to be accelerated toward the region of processing. For some embodiments, the tip has an end facet shape to function as a reflector for the particles. At least a portion of the tip may also be ablated by the radiation, the ablated portion of the tip being a source of particles for delivery to the region of processing. A unit may also be positioned between the tip and the region of processing which unit is ablated by radiation applied thereto to produce particles of ablation directed to the region of processing. A mechanism may be provided for advancing the portion of the unit between the tip and the region of processing as the unit is ablated. For preferred embodiments, the source of pulsed radiation is a pulsed laser.

The particles from the particle source are of a hardness which is at least close to that of the material in the region of processing and is preferably of a greater hardness. For preferred embodiments, the source of pulsed radiation is a pulsed laser.

A mechanism may also be provided for facilitating the removal of particles from an area between the tip and the area of processing, generally between radiation pulses. This mechanism may include a mechanism for vibrating the tip, the vibrations being preferably synchronized with the pulsed radiation to enhance particle delivery to the region of processing and/or the removal of particles. The mechanism for facilitating removal may alternatively include a mechanism for applying to the area between the tip and the area of processing a liquid, a gas, and/or underpressure to facilitate the removal of the particles. For certain embodiments, such delivery mechanism operates at least primarily between pulses from the source of pulsed radiation. Liquid and/or gas applied between pulses may also function to cool the surface of the area of processing. For another embodiment, air is applied before a radiation pulse to clean at least the area of processing, followed by a fine water spray or mist for at least cooling the region of processing, the radiation pulse occurring during the misting. The radiation pulse preferably lags the misting by at least a sufficient time for a thin water coating to form on the area of processing. The misting or a stronger water spray is applied after the radiation pulse.

The tip, instead of being solid, may be either hollow or liquid filled. A hollow tip may be shaped to minimize entry of particles from the particle source therein. The tip may also have an in facet cut at an angle to facilitate side processing of the material.

For preferred embodiments, the radiation is at a wavelength preferentially absorbed by the solid material. The radiation may also have a pulse duration which is of the same order or shorter than the thermal relaxation time of an absorbing fraction of the solid material. The distances between the end of the tip and a surface of the material to be processed is preferably not more than a distance of flight of the particles during which their speed decreases by a factor of 10.

The tip may be a dielectric waveguide with an end facet which is one of flat, elliptical and spherical. The tip may also include a microlens or may include some other portion focusing the radiation at or below the surface of the region of processing. A reflector may also be provided which surrounds the end of the tip and is shaped to direct the particles to the region of processing and to control the dimensions of such region.

As indicated earlier, for preferred embodiments, the solid material is a dental material such as dental enamel, dentine, bone, other dental tissue, filling material, cementum or stain. For such embodiments, the source of pulsed radiation is at a wavelength preferentially absorbed by such dental material. In particular, the source of pulsed radiation for such embodiments is preferably a pulsed laser. Examples of suitable pulsed lasers include Er:YAG with a wavelength of 2.94 $\mu$m, Er:YLF with a wavelength in the 2.71–2.87 $\mu$m range, Er:YGG with a wavelength of 2.7–2.8 $\mu$m, CTE:YAG with a wavelength in the 2.65–2.7 $\mu$m range, Ho:KGd (WO$_4$)$_2$ with a wavelength of 2.93 $\mu$m, and CO$_2$ with a wavelength in the 9–11 $\mu$m range.

The foregoing other objects, features and advantages will be apparent from the following more particular description of preferred embodiments as illustrated in the accompanying drawings, the same reference numeral being used for common elements in the various figures.

BRIEF DESCRIPTION OF THE DRAWINGS

FIG. 7a is a schematic representation of an embodiment of this invention which includes the additional application of spray and air-cooling systems.

FIGS. 7b and 7c are enlarged side and bottom views respectively of the tip for the embodiment shown in FIG. 7a.

DETAILED DESCRIPTION

The invention generally involves the recirculation of particles resulting from the ablation of a solid, preferably hard material, the essence of the invention involving the following:

Under ablation, normally laser ablation, the processed material in many cases breaks up into small-sized particles. This is characteristic of the case where the destruction begins with the heating of a strongly absorptive center inside the material. In this case, the pressure of the strongly heated up center results in the appearance of microcracks. In the paper "Human tooth in low and high intensive light fields" Proc. SPIE, v.2623, pp. 68–81, 1996 by G. Altshuler, this mechanism for the destruction of enamel or dentin under the influence of Er:YAG laser radiation is described. The cracking of enamel or dentin occurs as a result of the overheating of water inside the enamel's micropores or dentinal tubules. The products of ablation (particles) can be ejected from a zone of destruction with very high speed. For example, during the destruction of enamel by submillisecond pulses of Er:YAG laser, speeds for ablation products of 300 m/s, with sizes for particles of hydroxilapatite reaching 200 $\mu$m, have been measured. The most probable particle size is approximately 20 $\mu$m. The kinetic energy of such particles can be 0.5 mJ, which is enough for the destruction of enamel and dentin under collision.

During a laser pulse, the particles of processed material (for example enamel or dentin) being moved or deposited at an end facet of the waveguide can be ablated and accelerated by the same pulse. The particles of enamel and dentin at the moment of contact with the end facet of the waveguide can, due to strong absorption of light, blow up near the surface of the waveguide causing damage to the waveguide which results in the emission of fast particles of waveguide material. These secondary particles are accelerated by the laser radiation to increase the volume of material in collision with the processed material.

When the laser pulse is terminated, the particles of processed material (for example, enamel or dentin), can deposit on the surface of a dielectric, for example, the end facet of the waveguide. Therefore the next pulse can ablate and accelerate these particles. As a result of ablation, they move towards a processing zone of the material into collision with a surface of the processed material, resulting in additional destruction. These deposited particles can also cause the micro destruction of the surface of the dielectric (waveguide) and the particles of this dielectric destruction can be accelerated by the laser radiation in the direction of the processed material surface, causing additional destruction thereof. A unit of suitable material may also be mounted between the waveguide/tip of the processing zone and may be ablated by the laser to serve as an additional source of particles for destruction of the processed material surface.

Thus, the recirculation of the particles described above results in increased efficiency of processing, and this effect can be used for laser processing of dielectric crystals, polymers, polycrystalline materials, ceramics, composite materials and other hard materials. While the invention disclosed herein is used mainly for hard dental tissues or other dental materials, the invention is not limited in any way to this application and may be used for the materials indicated above and others.

Figure 1:
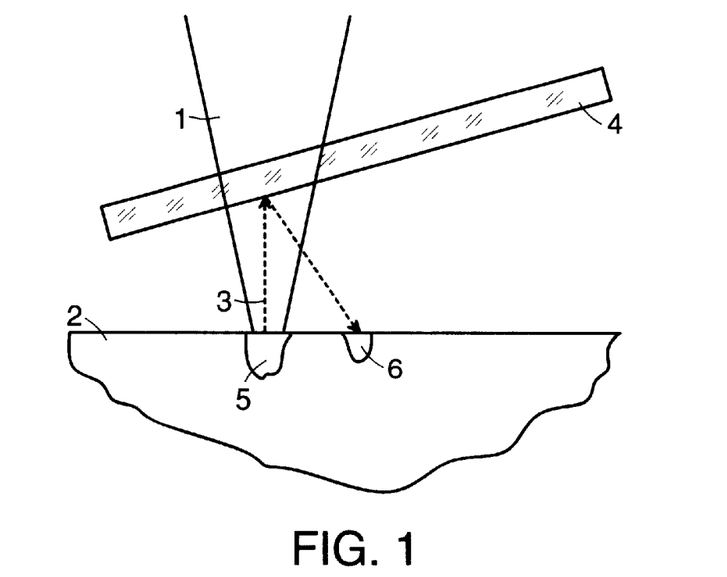
FIG. 1 and FIG. 2 are schematic diagrams of an experimental setup for the destruction of a substance using the energy of ablation products and the results of this processing respectively.
Figure 2:
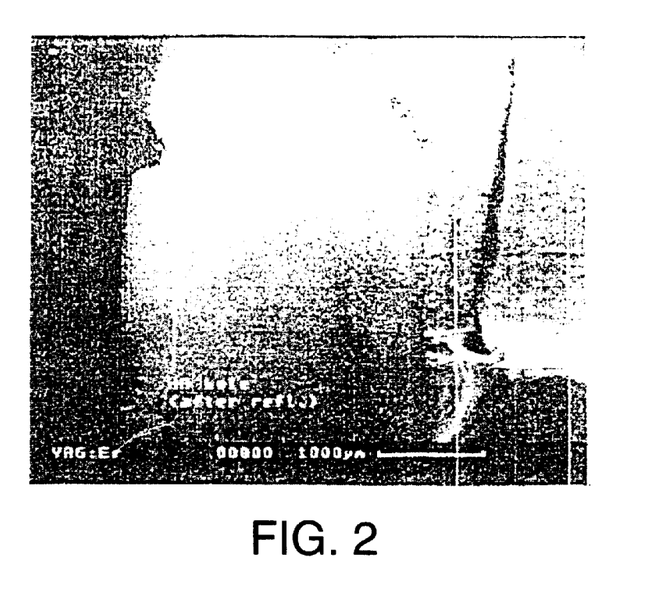

A schematic diagram of an experiment carried out to confirm the effects of the recirculation of particles is shown in FIG. 1. The beam 1 of Er:YAG laser radiation with a pulse energy of 0.3 mJ, pulse of duration 0.3. ms, and beam diameter of 0.6 mm ablated the enamel 2 of a human tooth. The products of ablation 3 (hydroxilapatite particles) hit the surface of a sapphire plate 4 positioned at an angle to the surface of enamel 2. The hydroxilapatite particles 3, having a lower hardness than sapphire, were reflected from the surface of plate 4 back to the surface of enamel 2, but in a zone 6 displaced from laser crater 5. As a result, there were two craters on the surface of enamel 2; laser crater 5 and crater 6 formed by the flow of fast enamel particles 3 reflected by sapphire plate reflector 4 (also see FIG. 2). The volume of crater 6 formed by the particles 3 is approximately the same as that of laser crater 5. Thus, particularly if there is overlapping of the craters, the efficiency of laser processing can be increased by at least a factor of two.

Figures 3A, 3B:
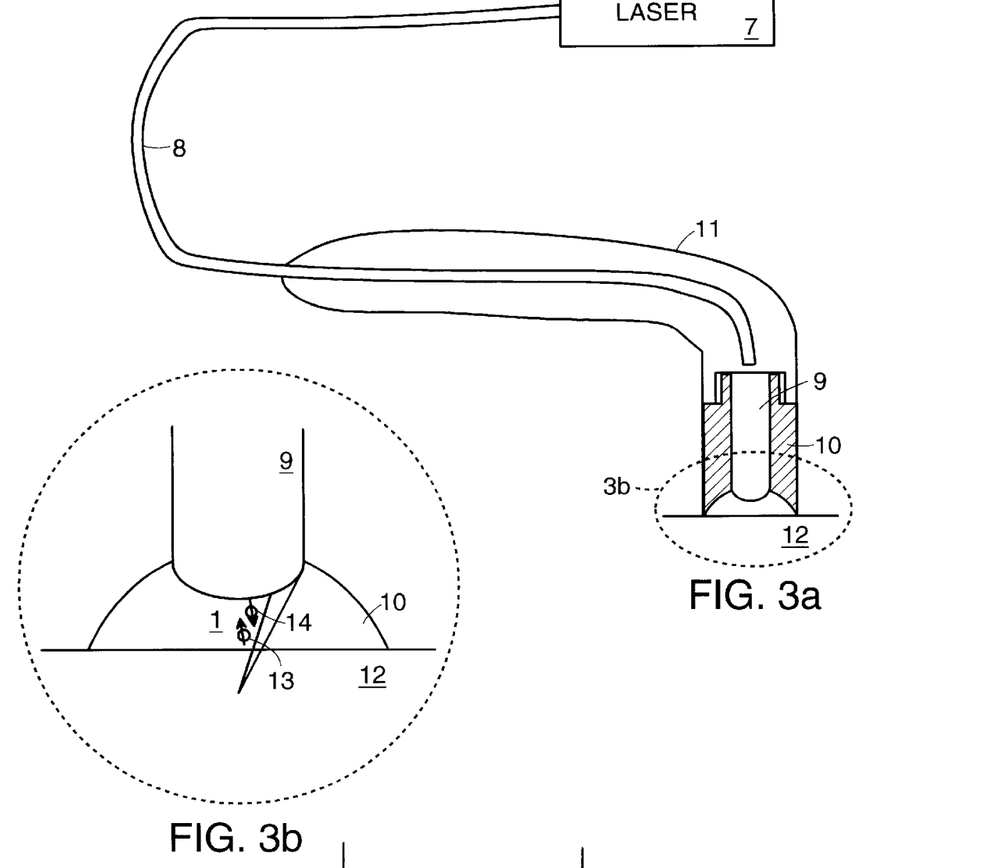
FIGS. 3a and 3b are semi-schematic side views of a device for the processing of materials in accordance with the teachings of this invention, including a particle reflector located around an output waveguide end facet and an enlarged view of the tip of the device, respectively.

The layout of an embodiment of the invention for material processing based on the effect of recirculation of particles is shown in FIGS. 3a and 3b. The device consists of a laser 7, a radiation delivery system shown as a light-guide 8 (for example, an optical fiber, hollow fiber, etc.), joined with an optical tip, shown as an output unit having a waveguide 9. A reflector 10 is located around waveguide 9. The output unit can be replaceable and easily disconnected from housing 11 by screw, bayonet or other conventional means. Waveguide 9 is made of a transparent material with a hardness which is preferably more than, but at least close to, the hardness of particles of the processed material, for example sapphire, quartz, glass, optical ceramics, and has a focusing or collimating surface on its leading edge. If reflector 10 returns particles to a processing zone of material 12, they destroy the material and produce new particles which are redirected to the processing zone by the reflector. Thus, this process of circulation of particles can repeat many times, increasing the efficiency of the process. Therefore, the effect is a recirculation of particles. Reflector 10 is made of a hard material providing elastic reflection of the particles, for example diamond, sapphire, metal, ceramics, metaloceramics. To increase the life-time of waveguide 9 and reflector 10, their surfaces facing processed material 12 can be covered with a film of a hard material, for example diamond, sapphire etc. In this case, the hardness of waveguide material 9 and reflector 10 can be lower than the hardness of processed material 12.

Figure 4:
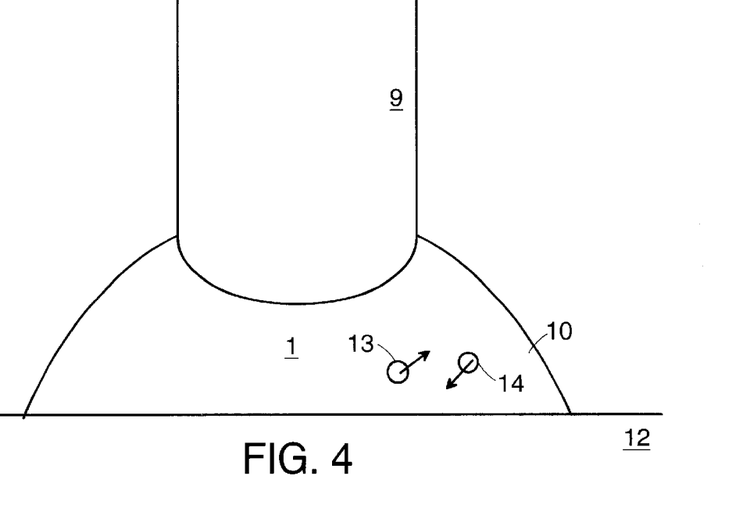
FIG. 4 is an enlarged view of a portion of FIG. 3 illustrating a scheme of reflector operation permitting regulation of the processing zone dimensions.

The form of the reflector and its orientation are selected to direct the flow of particles to a selected zone on a surface of the processed material. For example, the reflector surface can have the form of a hemisphere with a center concurrent with a focal point of radiation beam 1 and located inside the material near the processed surface thereof. In this case, ejected particles 13 are reflected back, mainly to the zone of laser ablation. If the center of the reflector orb 10 is displaced above the surface of processed material 12, the reflected particles 14 will hit on a surface of the processed zone mainly around the zone of laser effect. In this case, the transversal size of the processed zone will be enlarged (FIG. 4) (i.e., the damage zone for reflected particles will be around that for laser effect resulting in an enlarged cavity). By changing the form of the reflecting surface (plane, ellipse, hyperboloid, cone, cylinder, etc.) and the layout of the reflector, it is possible to control the dimensions of the processed zone. The reflection of particles is subject to the geometrical optics law; therefore the calculation for the optimization of the reflector is similar to that for the design of an optical system. It should also be noted that the beam and the reflector can have an axis of a symmetry (round beam) or a plane of symmetry (knife cut).

Figure 5:
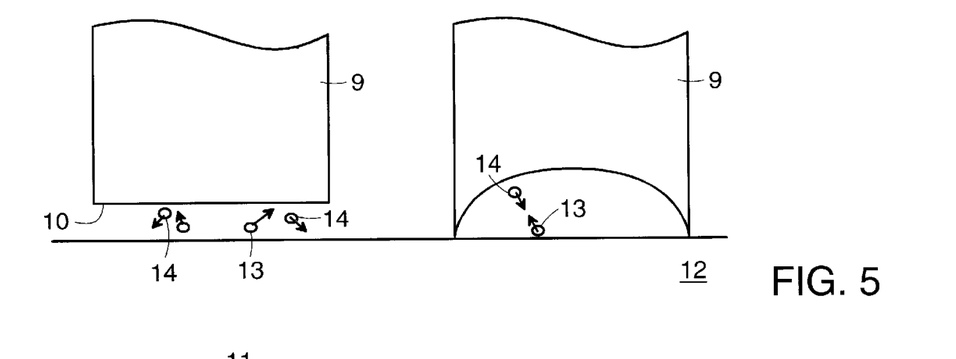
FIG. 5 illustrates the application of the output waveguide end facet as a reflector of particles.

An embodiment where the surface of the waveguide 9 functions as a reflector is shown in FIG. 5. In this case, the surface may be plane (FIG. 5a), spherical (FIG. 5b), conic, cylindrical, etc.

Figure 6:
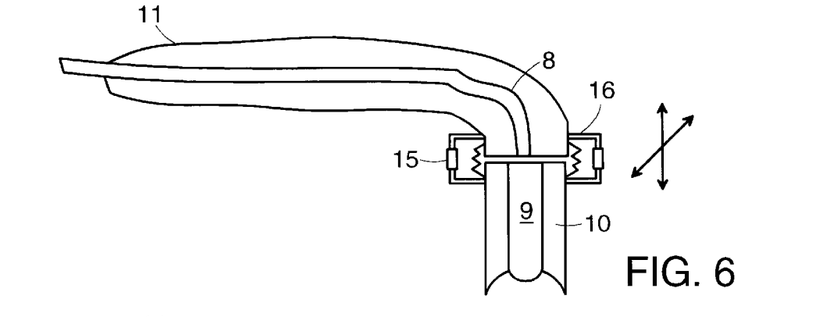
FIG. 6 is a schematic representation of an embodiment of the invention utilizing a vibrator for enhanced performance.

An embodiment where the reflector 10 and the waveguide 9 are attached to a vibrator 15 is shown in FIG. 6. The vibrator provides movement in a direction either perpendicular or parallel to the surface of the processed material. It may also provide turning around an axis laying in a plane parallel to the plane of the processed surface as well movements in this plane. The availability of these movements and turns allows the products of ablation to escape and thus not to be stored in the zone between the waveguide and reflector surfaces and the surface of material 12. If these particles cannot escape, they hinder the reflection of particles. The effect of particle removal can be enhanced if the movement of the tip is synchronized with the laser pulses so that the tip is moving towards the surface of the processed material during the ablation. Then the reflection of ablation products from the surface of the reflector increases their speed. The connection 16 provides air-tightness of the tip.

Figures 7A, 7B, 7C:
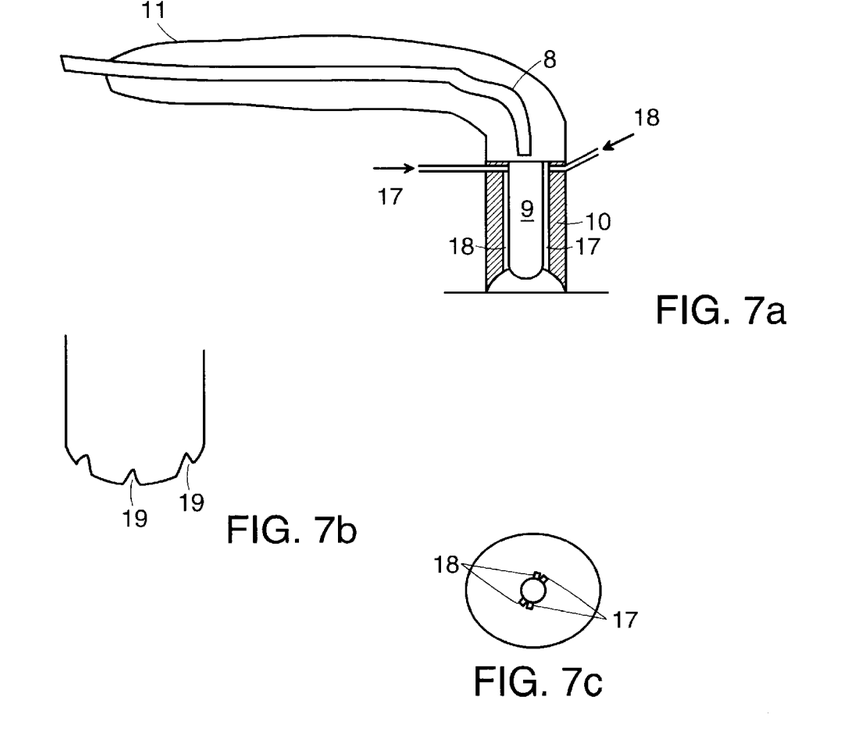

An embodiment where liquid or gas for cooling of processed material is supplied through channels 17, 18 to the zone of processing is shown in FIG. 7. The feeding of liquid or gas can take place between laser pulses so the speed of particles will not be reduced. The liquid and/or gas can also clean and protect the surface of the reflector and waveguide against the adhesion of particles. Underpressure/vacuum for the removal of the products of ablation may be supplied between pulses on the same channels. If underpressure is used, the channels are preferably designed so that either particles are not drawn therein, or if drawn therein, are returned. The underpressure also allows an increase in the speed of the recirculating particles because of decreased air resistance. Channels 17 and 18 can be closely located to the treatment area so a dispersion of particles of liquid will be produced, providing uniform fluid deposition on a cooled surface, and also to achieving a spray-effect (evaporation of small-size drops). To provide for the removal of liquid and products of ablation, small slits 19 can be made in the reflector. The removal of excess particles between pulses improves laser efficiency by as much as a factor of three. Channels 17 and 18 may have a spiral structure to provide more effective cooling of waveguide 9 and reflector 10. Gas or liquid can also enter in the space between lightguide 8 and waveguide 9 to cool their end facets.

For another embodiment, air is initially applied through a channel, for example channel 17, to clean the area of processing, the tip, the reflector, and/or the space between the tip and area of processing. A fine water spray or mist is then applied through the other channel, the laser/radiation source being fired during such misting. The misting cools the area of processing and lasts for a sufficient time before the radiation source is fired to provide a thin (for example one to 100 micron, preferably 10 micron) water coating on the area of processing, this water coating being ablated by the radiation to create a shock wave which can create microcracks in the material in the region of processing, facilitating the generation of the particles. The water mist is not heavy enough to interfere with the movement of particles of ablation. After the radiation pulse, either the water mist or a stronger water spray continues to be applied for a short period to cool and clean the area of processing. This sequence of operation may be repeated at the repetition rate of the radiation source, for example one Hz to fifty Hz. While the three step processed indicated above (i.e., air before the radiation pulse, misting before and during the pulse and mist/spray after pulse) are preferably employed together, one or more of these steps may be employed independently for selected embodiments. It is also possible for the water spray to be continuous, preferably with varying intensity, air for example being applied to the area of processing through the water mist.

Figure 8A:
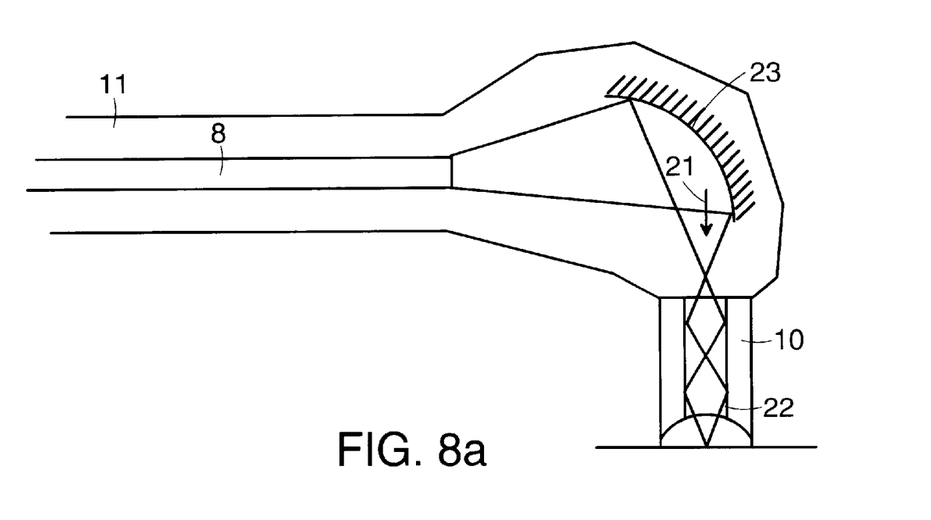
FIGS. 8a and 8b are schematic representations of two related embodiments of the invention which include a reflector of particles, where the output of the radiation delivery system is a mirror.
Figure 8B:
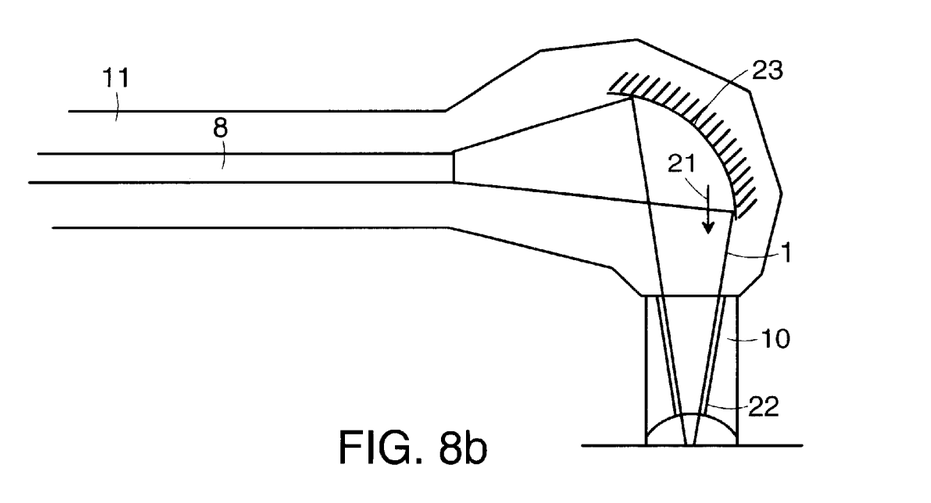

FIG. 8a is a schematic diagram of an optical tip with a waveguide output unit for an alternative embodiment. For this embodiment, waveguide 22 can be hollow or filled with liquid. In both cases, the waveguide 22 represents a cylindrical viahole (it can be a circular or elliptical cylinder). The lateral surface of the hole is polished to mirror quality or can be coated with a high-reflecting coating at the laser radiation wavelength. Radiation 21 from lightguide 8 of the radiation delivery system is directed to waveguide 22 by, for example, mirror 23. In order to prevent contamination of the walls of waveguide 22, liquid or gas can be passed through a hole as discussed above. The waveguide can be conic (FIG. 8b) where the concentration of radiation provided by the unit 23 (mirror or lens) takes place on a small square of the processed material (i.e., there is a small spot size). The conic form of the waveguide is adjusted to the shape of the radiation beam extending from mirror 23 to material 12, and the small size of the hole in the surface of reflector 10 limits the undesirable penetration of ablation products to mirror 23, and at the same time provides the desirable large reflecting surface.

Figures 9A, 9B:
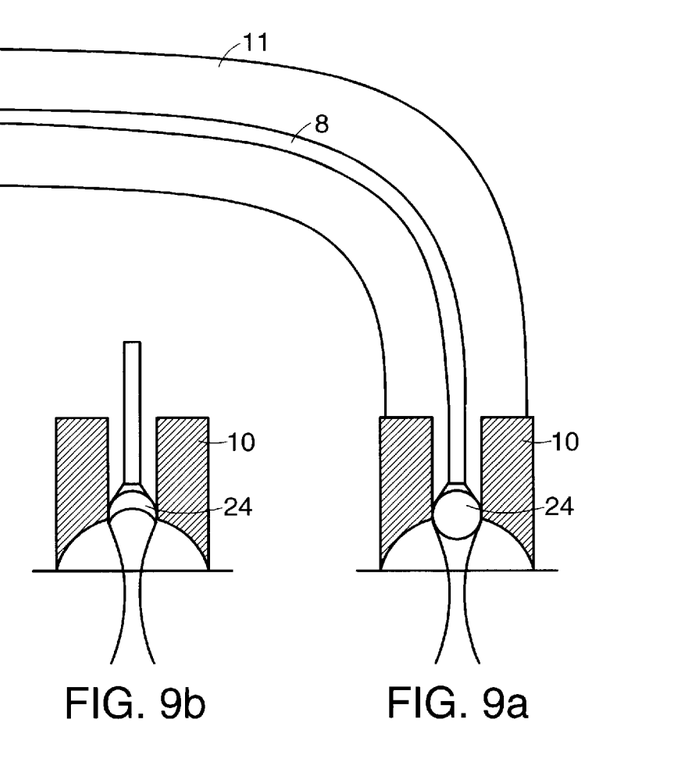
FIGS. 9a–9c show embodiments of the inventions with a reflector of particles, where the output of the radiation delivery system is a microlens.
Figure 9C:
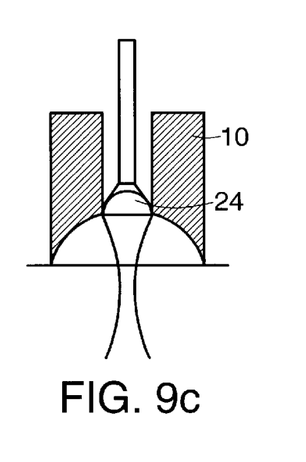

The layout of a tip with a microlens 24 as an output unit for concentration of radiation on the surface of the processed material is shown in FIG. 9. This microlens may be an orb (FIG. 9a), hemisphere (FIG. 9c) or meniscus (FIG. 9b) and may be formed from sapphire or other suitable material. The use of the microlens with plane, convex or concave surface faced to the surface of the processed material increases the concentration of particles reflected from the surface of the microlens. In order to reduce the effect of ablation particle adhesion to the surfaces of waveguide 9, microlens 24 and reflector 10, these surfaces can be coated with a material providing minimum adhesion with respect to the material of the ablation particles.

As mentioned above, the effect of particle recirculation consists of three parts: the first one is the reflection of ablation products back to the crater being formed in the processed material; the second is the acceleration of particles deposited on the end facet surface of waveguide 9 or lens 24 and on reflector 10 into the crater; and third is the acceleration of particles of material resulting from the ablation or destruction of surfaces of the waveguide 9, lens 24 or reflector 10 by laser radiation to the laser crater.

Figure 10:
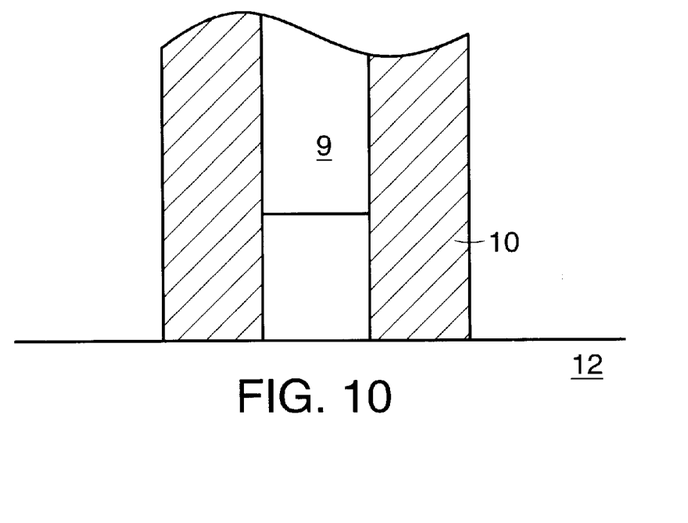
FIGS. 10–12 illustrate three further embodiments of apparatus for use in practicing the teachings of the invention.

In all the versions of the devices shown in FIGS. 3–9, and in particular FIG. 5, two of these parts may play an essential role. In these devices, the reflector 10 and end facet of the waveguide 9 or lens 24 function as a repository for particles which have left the laser crater, but which on reaching the waveguide, reflector or lens do not have sufficient energy to be reflected, and therefore adhere to the surface. The construction of a tip in which particles of ablated material can deposit on the surfaces of waveguide 9 and reflector 10 is shown in FIG. 10. These surfaces thus simultaneously serve as a repository of the particles. Such adhesion often occurs at the end of a pulse when energy is reduced.

Laser radiation passing through the surface of waveguide 9, for example from the next pulse, and being reflected from the surface of the reflector 10, ablates the deposited particles of processed material, creating pressure which initiates particle movement towards the surface of processed material 12 where the particles cause additional destruction.

Figure 11:
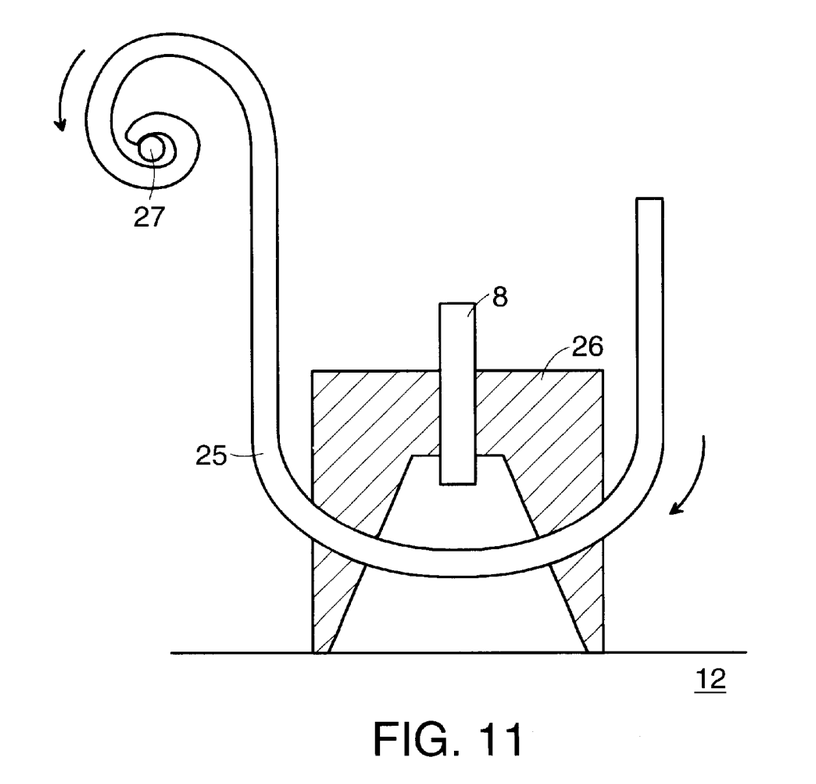

An embodiment where a third mechanism for producing recirculating particles is used is shown in FIG. 11. Radiation from light-guide 8 hits on a floppy film, fiber or other unit 25 of a composite material formed at least in part of a hard material such as sapphire particles. Unit 25 can be an optical fiber made of a material which is partially or completely absorbed by the laser radiation, for example quartz, glass or sapphire, or a film coating of the same material. The width of unit 25 can be less than that of the radiation so that, even if the unit is fully absorptive, radiation reaches the area of processing. Thus, radiation may reach the area of processing for this embodiment through a unit which is at least partially transparent and/or around the unit. The light-guide 8 and floppy unit 25 are fixed in a housing 26 which can function as a reflector. During each laser pulse, partial ablation of the material of the unit 25 from its surface facing the processed material 12 takes place, this ablation accelerating the particles toward material 12. Unit 25 should include a material having a hardness which is at least close to and preferable more than the hardness of the processed material. Ablation of the material of unit 25 takes place because of absorption of laser radiation by its surface and/or due to absorption of radiation by the products of ablation of the processed material which are deposited on the surface of this unit. The particles of material from unit 25 cause additional removal of processed material 12. Since unit 25 can be damaged during each pulse, a system 27 is provided for continuous or discrete moving of unit 25 between pulses. System 27 can, for example, be represented by a motor having an axis or shaft on which unit 25 can be reeled. If unit 25 is formed as a cylindrical waveguide, it can also focus laser radiation on the surface of the processed material.

Figure 12A:
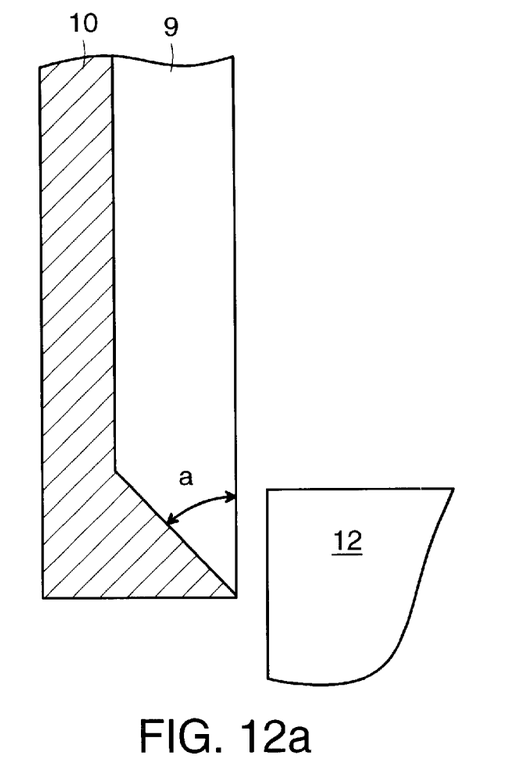
Figure 12B:
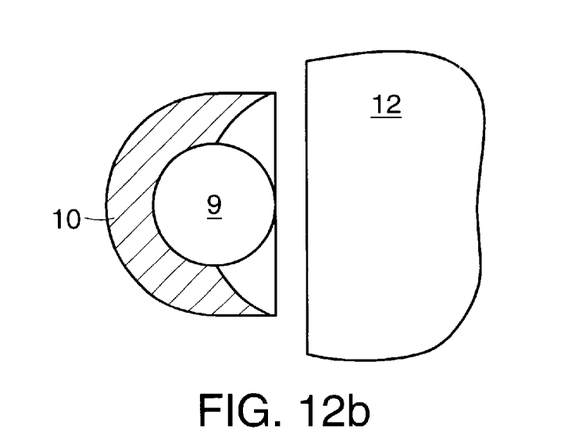

An embodiment having an output unit with a tip providing side processing of the material is shown in FIG. 12. In dentistry, such kind of treatment is necessary, for example, for the processing of a tooth before crown making. In this case, waveguide 9 is made with an edge cut angle "a" of 20°<a<60°. The waveguide is placed in reflector 10 with the reflecting surface parallel to the surface of processed material 12. In this case, low energy particles can adhere to a lateral area of waveguide 9 faced to the surface of material 12, and can be accelerated to the surface of material 12 by the next laser pulse in the manner previously described.

All the tips for the embodiments described above, when used in dentistry or certain other applications, can be made as one-time appliances, limited use appliances or extended use appliances, a softer tip being used for a one-time tip, and the hardness of the tip increasing as the projected use for the tip increases. In particular, in addition to obtaining particles from the processed material and/or from a unit 25 as shown in FIG. 11, particles may also be obtained from the tip. This can happen in a number of ways. First, as indicated earlier, low energy particles may adhere to the tip, particularly near the end of a light pulse. Such particles may then be ablated and/or accelerated by the next laser/radiation pulse and can cause part of the tip to be removed with them when ablated. Alternatively, particularly if a softer tip is used, high energy particles and ablating on the tip may cause particles to break off from the tip, which particles can be accelerated to the surface of processed material 12. Similarly, reflector 10 may also be formed of a materials of varying hardness depending on the extent of use desired for the reflector. The reflector may also serve as a source of particles based on mechanisms similar to those discussed above with respect to the tip. Finally, depending on the material of the tip 9, the radiation passing through the tip may cause some ablation thereof resulting in additional particle production.

In order to realize the recirculation of particles, the radiation wavelength, pulse duration and energy density should be set within defined ranges. The wavelength should be within the range of maximum absorption of the processed material or a selected portion thereof. The pulse duration should be of the same order or shorter than the time of thermal relaxation of the absorbing fraction or layer of the processed material with a thickness which is approximately the depth of light penetration in the material. The density of pulse energy should be sufficient for destruction of the material by microexplosions. The indicated parameters can be found for each processed material. Considering enamel, dentin and bone tissues, the wavelength of radiation should correspond to wavelengths strongly absorbed by the main components of hard tissues: water, hydroxilapatite and/or proteins. The range of wavelengths should be 1.9–2.1 $\mu$m (water), 2.65–3.5 $\mu$m (water, hydroxilapatite, proteins), 5.6–7.5 $\mu$m (proteins), 8.5–11 $\mu$m (water, hydroxilapatite). Therefore, for example, holmium, erbium, CO and $CO_2$ lasers can be used. The duration of pulses depends on the dimensions of the absorbing components—drops of water 0.01–10 $\mu$m, or water inside the dentinal tubules 1–10 $\mu$m, enamel prisms, interprismatic spaces 1–20 $\mu$m, collagen clusters 0.1–10 $\mu$m, and is normally within a 0.0001–1000 $\mu$s range. The preferable range is 1–500 $\mu$s. Experiments show that the energy density should be within the 0.5–500 J/cm$^2$ range (5–150 J/cm$^2$ range is preferable). An important parameter of the invention is the distance S between the processed surface and the surface of the waveguide 9. This distance should not be more than the length of particle flight during which the speed of the particle decreases by more than a factor of ten. The decrease of speed takes place due to friction of the particles moving in air; this decrease in particle speed can be reduced by providing reduced pressure or vacuum condition in the space between the reflector/waveguide and the processed material. The distance S can be determined according to the formula $S=V_0/2\gamma(1-e^{-\gamma})$, where $\gamma=18\eta/\rho d^2$, $\eta$=viscosity of air, $\rho$=density of particle material, d=particle diameter, $V_0$=initial speed of particles. Applying the formula for hard tissues, S should be within the 0–10 mm range. The preferable range is 0.1 mm.

Where the invention is being utilized for the removal of hard dental tissues (for example, enamel, dentin, cement, and also tooth stains and filing materials (including composites), laser 7 can be a laser generating radiation in the spectral range 2.69–3 $\mu$m. In particular, it may be an Er:YAG laser or a laser based on Er:YSGG, Er:YLF, Er:YAP, Er:Cr:YAG or an ions Ho:KGd $(WO_4)_2$. $CO_2$ laser. The radiation from the laser can be delivered to the tip via a solid waveguide, hollow waveguide with a solid tip or via an optical system. The laser may be placed directly inside a tip; the pumping radiation in this case can be the radiation of another laser, for example a diode laser or solid-state laser transmitted through the waveguide. The laser can also be made as a waveguide with a core doped by the ions, for example, of erbium. Optical radiation sources other than lasers, for example flash lamps/arc lamps, may also be utilized in practicing the teachings of this invention in appropriate applications, particularly non-dental applications.

While the invention has been described above primarily with respect to embodiments for performing drilling or other processing on dental tissue and/or other dental materials, the invention is in no way limited to such applications and may, for example, be used in various orthopedic applications for drilling or otherwise processing bone or other hard tissue or may be used in a wide variety of applications where solid, generally hard material such as metals, ceramic, glass, crystals, various composites certain plastics and the like are to be drilled or otherwise processed. Further, while the invention has been discussed with respect to a number of preferred embodiments, and variations on the embodiments have also been discussed, it is to be understood that these embodiments are for purposes of illustration only and that the invention is to include the foregoing and other changes in form and detail which might be apparent to one skilled in the art and is to be limited only by the following claims.

What is claimed is:

1. A device for processing a hard solid material including:
   a source of pulsed radiation;
   at least one source of particles having a hardness which is at least close to that of said material; and
   a system for delivering radiation from said source to a region of processing of said solid material, said system system comprising a tip, including an end for delivering radiation, radiation accelerating particles from said at least one particle source, which particles are at least one of accelerated to and reflected to a region of processing on a surface of said solid material to influence the processing thereof.

2. A device as claimed in claim 1 wherein said at least one particle source is said region of processing on the surface of said solid material, said radiation ablating said surface to create particles accelerated away from said surface, and said system including a reflector, at least some of said accelerating particles being reflected back to said region of processing by at least one of said tip and said reflector to further process said surface.

3. A device as claimed in claim 2 wherein the radiation and the reflected at least some of said accelerating particles impinge on substantially a single point on said surface in said region of processing.

4. A device as claimed in claim 2 wherein the radiation and the reflected at least some of said accelerating particles impinge on different points on said surface in said region of processing.

5. A device as claimed in claim 2 wherein, at the end of at least some radiation pulses, some particles of ablation adhere to said tip, and wherein said adhered particles are an additional particle source for a subsequent radiation pulse, at least some of said adhered particles being ablated by said subsequent radiation pulse so as to be accelerated towards said region of processing.

6. A device as claimed in claim 2 wherein said tip has an end facet shaped to function as a reflector for said accelerating particles.

7. A device as claimed in claim 1 wherein at least a portion of said tip is ablated by said radiation, the ablated portion of said tip being a particle source for delivery to said region of processing.

8. A device as claimed in claim 1 wherein said at least one source of particles includes a unit positioned between said tip and said region of processing, said unit being ablated by radiation applied thereto to produce particles of ablation directed to said region of processing.

9. A device as claimed in claim 8 including a mechanism for advancing a portion of said unit between said tip and region of processing as the unit is ablated.

10. A device as claimed in claim 1 wherein said source of pulsed radiation is a pulsed laser.

11. A device as claimed in claim 1 wherein said particles have a hardness greater than that of said material in the region of processing.

12. A device as claimed in claim 1 including a mechanism for facilitating the removal of said particles from an area between said tip and said region of processing between radiation pulses.

13. A device as claimed in claim 12 including a mechanism which vibrates the tip.

14. A device as claimed in claim 13 wherein vibration of the tip is synchronized with pulsed radiation from said source to enhance at least one of delivery of said particles delivery to the region of processing and the removal of said particles.

15. A device as claimed in claim 12 wherein said mechanism for facilitating removal includes a mechanism for applying to said area at least one of a liquid, a gas and an underpressure to facilitate the removal of said particles.

16. A device as claimed in claim 15 wherein said mechanism for applying is at least primarily operative between pulses from said source of pulsed radiation.

17. A device as claimed in claim 1 wherein said tip is hollow, said radiation being directed therethrough to said region of processing.

18. A device as claimed in claim 17 wherein said hollow tip is shaped to minimize entry of particles from said at least one particle source therein.

19. A device as claimed in claim 1 wherein said tip has an end facet cut at an angle to facilitate side processing of the material.

20. A device as claimed in claim 19 wherein said angle is 20° to 60°.

21. A device as claimed in claim 1 wherein the radiation from said source is of a wavelength preferentially absorbed by said solid material.

22. A device as claimed in claim 21 wherein radiation from said source has a pulse duration which is of the same order or shorter than the thermal relaxation time of an absorbing fraction of said solid material.

23. A device as claimed in claim 1 wherein a distance between the end of said tip and a surface of said material to be processed is not more than a distance of flight of said particles during which particle speed decreases by a factor of ten.

24. A device as claimed in claim 1 wherein said tip includes a dielectric waveguide with a facet which is one of plane, conic, cylindrical and spherical.

25. A device as claimed in claim 1 wherein said tip end includes a microlens.

26. A device as claimed in claim 1 wherein said tip includes a portion focusing said radiation at or below a surface of said region of processing.

27. A device as claimed in claim 1 including a mechanism for applying at least one of a liquid and a gas to cool said region of processing.

28. A device as claimed in claim 1 including a reflector surrounding the end of the tip and said reflector shaped to direct the particles to said region of processing and to control dimensions of said region.

29. A device as claimed in claim 1 including a mechanism applying a fine water spray or mist to said region of processing during radiation pulses from said source.

30. A device as claimed in claim 29 wherein said mechanism also applies said fine water spray or mist for a period prior to each radiation pulse sufficient for a thin coating of water to form on said region of processing.

31. A device as claimed in claim 29 including a mechanism for applying air to said region of processing prior to each radiation pulse.

32. A device as claimed in claim 29 including a mechanism for applying a water spray to said region of processing after each radiation pulse.

33. A device as claimed in claim 1 wherein said solid material is at least one of dental enamel, dentin, bone, other dental tissue, filling material, cementum and stain.

34. A device for processing dental material including at least one of dental enamel, dentin, bone, other dental tissue, filling material, cementum and stain, comprising:
a source of pulsed radiation at a wavelength preferentially absorbed by the dental material;
a source of particles which has a hardness which is at least close to that of said dental material in a region of processing; and
a system delivering radiation from said source of pulsed radiation to a region of processing on a surface of said dental material to at least partially influence the processing thereof, radiation also being delivered to said source of particles to accelerate particles therefrom, said particles being at least one of accelerated to and reflected to the region of processing to further influence said processing.

35. A device as claimed in claim 34 wherein said particle source is said region of processing on the surface of said dental material, said radiation ablating said surface to create particles accelerated away from said surface, at least some of said accelerating particles are reflected back to a region of processing by at least one of said tip for delivering radiation on said system and reflector to further process said surface.

36. A device as claimed in claim 35 wherein, at the end of at least some radiation pulses, some particles of ablation adhere to said tip, and wherein said adhered particles are an additional particle source for a subsequent radiation pulse, at least some of said adhered particles being ablated by said subsequent radiation pulse so as to be accelerated towards said region of processing.

37. A device as claimed in claim 35 wherein at least a portion of said tip ablated by said radiation, the ablated portion of said tip being a particle source for delivery to said region of processing.

38. A device as claimed in claim 35 wherein said source of particles includes a unit positioned between said tip and said region of processing, said unit being ablated by radiation applied thereto to produce particles of ablation directed to said region of processing.

39. A device as claimed in claim 35 including a mechanism for facilitating the removal of said particles from an area between said tip and said region of processing between radiation pulses.

40. A device as claimed in claim 35 wherein said tip has an end facet cut at an angle to facilitate side processing of the dental material.

41. A device as claimed in claim 40 wherein said angle 20° to 60°.

42. A device as claimed in claim 34 wherein said source of pulsed radiation is a pulsed laser.

43. A device as claimed in claim 42 wherein the pulsed laser is one of Er:YAG with a wavelength of 2.94 $\mu$m, Er:YLF with a wavelength in the 2.71–2.87 $\mu$m range, Er:YGG with a wavelength of 2.7–2.8 $\mu$m, CTE:YAG with a wavelength in the 2.65–2.7 $\mu$m range, Ho:KGd(WO$_4$)$_2$ with a wavelength of 2.93 $\mu$m, and CO$_2$ with a wavelength in the 9–11 $\mu$m range.

44. A device as claimed in claim 34 including a mechanism for cooling said dental material.

45. A method of processing dental material including at least one of dental enamel, dentin, bone, other dental tissue, filling material, cementum and stain, comprising:

exposing the dental material to pulsed radiation to influence the processing thereof in a region of processing;

utilizing the pulse radiation to generate particles of ablation; and reflecting directing said particles of ablation to said region of processing of the dental material to further influence processing thereof.

46. A method as claimed in claim 45 wherein said pulsed radiation is of an energy above an ablation threshold for the dental material.

47. A method as claimed in claim 46 wherein some particles of ablation are deposited on a surface adjacent said region of processing.

48. A method as claimed in claim 45 including at least one of a tip and an extra piece of material through said radiation passes and which is partially abated during said utilizing step to generate additional particles reflected during said reflecting step to said region of processing.

49. A method as claimed in claim 45 wherein said pulsed radiation is from a laser with a wavelength within one of 1.91–2.1 $\mu$m, 2.65–3.5 $\mu$m, 5.6–7.5 $\mu$m, and 8.5–11 $\mu$m; a duration of 0.0001–10000 $\mu$s; and an energy density of 0.5–500 J/cm$^2$.

50. A method as claimed in claim 45 including at least one of cooling the region of processing of said dental material and removing said particles from an area between a source of said pulsed radiation and said region of processing between pulses of said radiation.

51. A method as claimed in claim 45 including directing a fine water spray or mist at said region of processing during each pulse of said radiation.

52. A method as claimed in claim 51 wherein said directing a fine water spray or mist step lasts for a sufficient period prior to each radiation pulse for a thin water coating to be formed on said region of processing.

53. A method as claimed in claim 45 including at least one of directing air at said region of processing before each pulse of said radiation and directing a water spray to said region of processing after each said pulse.

* * * * *